US006818630B1

(12) United States Patent
Duncan et al.

(10) Patent No.: US 6,818,630 B1
(45) Date of Patent: Nov. 16, 2004

(54) BIOLOGICALLY ACTIVE MATERIALS

(75) Inventors: Ruth Duncan, Cardiff (GB); Dale Hreczuk-Hirst, London (GB); Lisa German, London (GB)

(73) Assignee: ML Laboratories PLC, London (GB)

( * ) Notice: Subject to any disclaimer, the term of this patent is extended or adjusted under 35 U.S.C. 154(b) by 0 days.

(21) Appl. No.: 10/018,608

(22) PCT Filed: Jun. 19, 2000

(86) PCT No.: PCT/GB00/02216

§ 371 (c)(1),
(2), (4) Date: Jul. 30, 2002

(87) PCT Pub. No.: WO00/78355

PCT Pub. Date: Dec. 28, 2000

(30) Foreign Application Priority Data

Jun. 18, 1999 (GB) .............................................. 9914187
Dec. 22, 1999 (GB) .............................................. 9930252

(51) Int. Cl.$^{7}$ .......................... A61K 31/70; C07H 15/00
(52) U.S. Cl. ............................ 514/58; 536/46; 536/103
(58) Field of Search .............................. 514/58, 34, 23, 514/37, 53; 536/46, 103, 6.4; 424/78.18, 486, 488

(56) References Cited

FOREIGN PATENT DOCUMENTS

| | | |
|---|---|---|
| EP | 0477931 A1 | 4/1992 |
| WO | WO 95/05199 | 2/1995 |
| WO | WO 96/35720 | 11/1996 |
| WO | WO 98/56424 A | 12/1998 |

OTHER PUBLICATIONS

Shen et al., "cis–Aconityl spacer between daunomycin and macromolecular carriers: a model of pH–sensitive linkage releasing drug from a lysomotropic conjugate" Biochemical and Biophysical Research Communications, US, Academic Press Inc., vol. 102, No. 3, Oct. 15, 1981, pp. 1048–1054.

Hreczuk–Hirst et al., "Synthesis and characterisation of dextrin–doxorubicin conjugates: A new anticancer treatment" Proceedings of the Int'l. Symp. Control. Rel. Bioact. Society, Inc., Jul., 1999, vol. 26, pp. 1086–1087.

Arranz, et al., "Adducts of Succinylated Dextran–Benzocaine. Synthesis and Controlled Release Behaviour." Makromolekulare Chemie, Rapid Communications, CH, Huthi Und WePf Verlag. Basel, vol. 13, No. 9, Sep. 1, 1992, pp 403–407.

*Primary Examiner*—Elli Peselev
(74) *Attorney, Agent, or Firm*—Klarquist Sparkman, LLP

(57) ABSTRACT

The present disclosure concerns biologically active materials, particularly materials that comprise a biodegradeable polymer linked to a biologically active agent. The disclosure further concerns materials known as polymer-drug conjugates that typically contain a therapeutic agent, for instance a bioactive cytotoxic drug linked to a polymer backbone. The linkage typically is a convalent linkage. However, in some embodiments the disclosure concerns other polymer conjugates including those where the biologically active agent is an imaging agent, such as a tyrosinamide, a diagnostic agent, or a targeting agent, such as biotin.

20 Claims, 6 Drawing Sheets

| Degree of Succinoylation | % Reduction of peak mass of primary peak | |
|---|---|---|
| | 60 min | 180 min |
| 0 | 84 | 99 |
| 5 | 85 | 90 |
| 5 (6 wt % Dex) | 77 | 92 |
| 15 | 49 | 75 |
| 34 | 0 | 20 |

n=3 ±S.D.

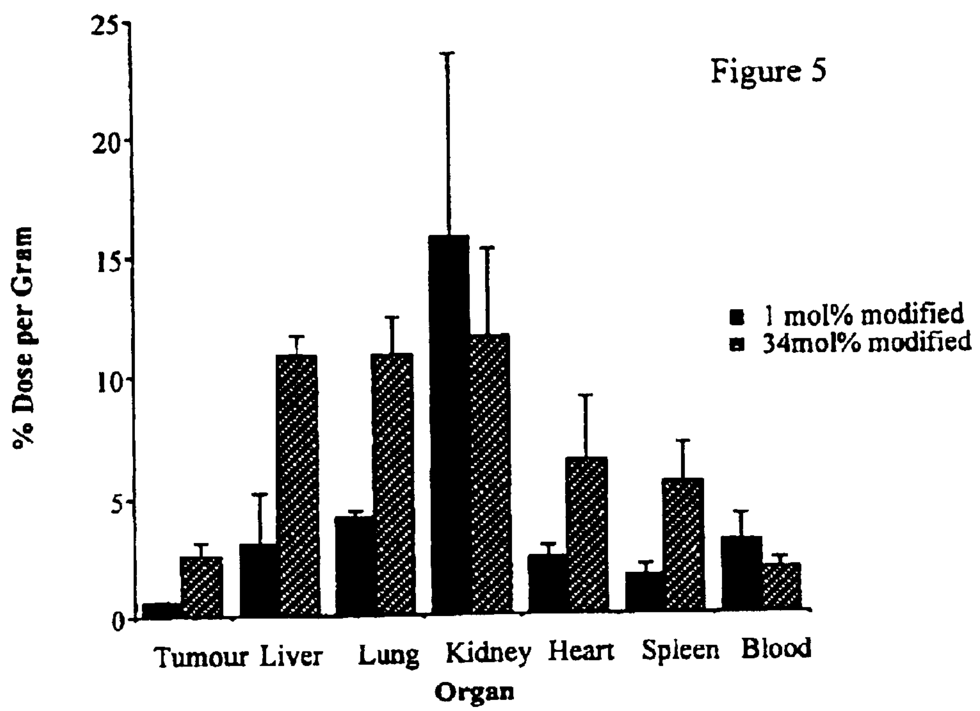
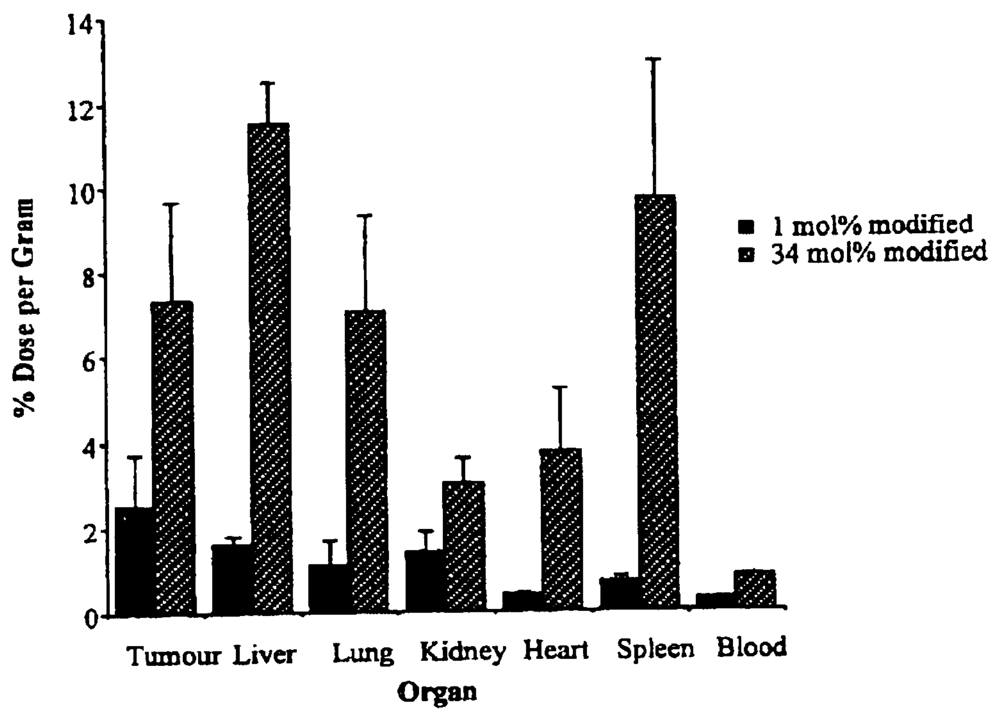
Figure 6

BIOLOGICALLY ACTIVE MATERIALS

FIELD OF INVENTION

This invention relates to biologically active materials and, in particular, to materials which comprise a biodegradable polymer linked to a biologically active agent. The invention is concerned with materials known as polymer-drug conjugates which typically contain a therapeutic agent for instance, a bioactive cytotoxic drug, linked to a polymer back-bone. The linkage between the polymer and the drug is typically by covalent bonding. However, the invention is applicable to other polymer conjugates including those where the biologically active agent is an imaging agent, such as tyrosinamide, a diagnostic agent, or a targeting agent such as biotin.

Reference will be made hereinbelow to polymer-drug conjugates in which the drugs are anticancer agents. However, the present invention has application in connection with other drugs and/or bioactive agents.

BACKGROUND OF THE INVENTION

In designing a polymer-drug conjugate, the aim is to deliver a drug effectively to a therapeutic site such as a tumour. It is known, for instance, that polymer-drugs given intravenously can accumulate selectively in solid tumour tissue by the EPR effect.

The most commonly used anticancer agents are low molecular weight compounds which readily gain access to cells by rapid passage across the cell membrane. After intravenous (IV) administration, a large percentage of the injected dose leaves the circulation within a few minutes, resulting in a ubiquitous body distribution of drug and little selective concentration in tumour tissue. By creating a macromolecular polymer-anticancer drug conjugate, there is provided an opportunity to improve tumour specific targeting, to minimise drug entry into sites of toxicity, to control precisely the rate of drug liberation at the target site (giving opportunities for long-term controlled release) and to deliver the active principal intracellularly, thereby providing a means to overcome p-glycoprotein related multi-drug resistance.

Numerous polymers have been proposed for synthesis of polymer-drug conjugates including polyaminoacids, polysaccharides such as dextran, and synthetic polymers such as N-(2-hydroxypropyl)methacrylamide (HPMA) copolymer. However, these polymers have limitations. For example, a dextran-doxorubicin conjugate has been tested clinically and been found to be much more toxic than the parent drug. Furthermore the HPMA copolymers which have been clinically tested have the disadvantage of being non-biodegradable in the main chain.

WO-A-98/56424 discloses a polymer-drug conjugate in which the polymer is the polysaccharide dextrin. Such a polymer-drug conjugate may be prepared in various ways. One method involves succinoylating dextrin and reacting the succinoylated dextrin with the drug or a reactive derivative thereof.

WO-A-98/56424 includes an example in which the extent of succinoylation of dextrin varies from 2.26 to 6.64 Mol %. In a further example the drug doxorubicin is conjugated to succinoylated dextrins in which the extent of succinoylation varies from 0.5 to 14.9 Mol %.

WO-A-98/56424 also includes examples showing the rate of degradation of dextrin both in the absence and in the presence of appropriate enzymes and also in rat plasma.

For at least certain applications the rate of degradation of dextrin in a dextrin-drug conjugate is an important consideration. For instance, it may be desirable to have a relatively slow rate of degradation in some applications while in other applications a faster rate of degradation is either acceptable or indeed even preferred.

STATEMENT OF INVENTION

It has now been surprisingly discovered that the rate of dextrin degradation is highly dependent on the degree of dextrin backbone substitution. As a result, it is possible to tailor the dextrin by appropriate substitution of its backbone in order to achieve a desired rate of degradation.

According to a first aspect of the invention there is provided a polymer drug conjugate comprising:

i) at least one anti-cancer drug; and ii) a dextrin polymer characterised in that said dextrin polymer is modified by the addition of pendent groups so that the stability of the polymer drug conjugate is enhanced.

The term "dextrin" means a glucose polymer which is produced by the hydrolysis of starch and which consists of glucose units linked together by means mainly of alpha-1,4 linkages. Typically dextrins are produced by the hydrolysis of starch obtained from various natural products such as wheat, rice, maize and tapioca. In addition to alpha-1,4 linkages, there may be a proportion of alpha-1,6 linkages in a particular dextrin, the amount depending on the starch starting material. Since the rate of biodegradability of alpha-1,6 linkages is typically less than that for alpha-1,4 linkages, for many applications it is preferred that the percentage of alpha-1,6 linkages is less than 10% and more preferably less than 5%.

Any dextrin is a mixture of polyglucose molecules of different chain lengths. As a result, no single number can adequately characterise the molecular weight of such a polymer. Accordingly various averages are used, the most common being the weight average molecular weight (Mw) and the number average molecular weight (Mn). Mw is particularly sensitive to changes in the high molecular weight content of a polymer whilst Mn is largely influenced by changes in the low molecular weight of the polymer.

It is preferred that the Mw of the dextrin is in the range from 1,000 to 200,000, more preferably from 2,000 to 55,000.

The term 'degree of polymerisation' (DP) can also be used in connection with polymer mixtures. For a single polymer molecule, DP means the number of polymer units. For a mixture of molecules of different DP's, weight average DP and number average DP correspond to Mw and Mn. In addition DP can also be used to characterise a polymer by referring to the polymer mixture having a certain percentage of polymers of DP greater than a particular number or less than a particular number.

It is preferred that, in the dextrin-drug conjugate of the present invention, the dextrin contains more than 15% of polymers of DP greater than 12 and, more preferably, more than 50% of polymers of DP greater than 12.

Modifications to dextrin may be negatively charged groups, neutral groups or positively charged groups, (eg quaternary ammonium groups).

In a further preferred embodiment of the invention said dextrin modification is succinoylation.

In a yet further preferred embodiment of the invention said dextrin succinoylation is greater than 20 mol %. Preferably said dextrin succinoylation is at least 30 mol %. More prefereably still said succinoylation is from 30% to 40%.

More preferably still said succinoylation is 30 mol %; 31 mol %; 32 mol %; 33 mol %; 34 mol %; 35 mol %; 36 mol %; 37 mol %; 38 mol %; 39 mol %; 40 mol %. Ideally said succinoylation is 34 mol %.

In a yet further preferred embodiment of the invention said succinoylated dextrin comprises an anti-cancer agent selected from: cyclophosphamide; melphalan; carmusline; methotrexate, 5-fluorouracil; cytarabine; mercaptopurine; anthracyclines; daunorubicin; doxorubicin; epirubicin; vinca alkaloids; vinblastin; vincristine; dactinomycin; mitomycin C; taxol; L-asparaginase; G-CSF; cisplatin; carboplatin.

More preferably still said anti-cancer agent is doxorubicin.

According to a further aspect of the invention there is provided a pharmaceutical composition comprising a polymer drug conjugate according to any previous aspect or embodiment of the invention.

In a preferred embodiment of the invention said composition comprises a diluent, carrier or excipient.

In a further preferred embodiment of the invention said polymer drug conjugate is for use in the manufacture of a medicament for the treatment of cancer.

According to a further aspect of the invention there is provided a method to treat an animal, ideally a human being, suffering from cancer by administration of the polymer drug conjugate according to the invention.

It has been found that, in the case of substitution of the dextrin backbone by succinoylation, relatively rapid degradation takes place at a degree of succinoylation of up to about 15%. By contrast a degree of succinoylation above 30% very markedly reduces the rate of degradation.

The present invention provides a dextrin-drug conjugate in which the degree of substitution of the dextrin chain is greater than 15%, more preferably greater than 20% and most preferably greater than 30%.

The drug of the dextrin-drug conjugate may be loaded on the polymer via a linking group, such as succinoyl, in which case it may be attached to some or all of the linking groups. Alternatively the drug may be directly loaded onto the dextrin backbone in which case the drug itself acts as the substituting group. As a further possibility the drug may be loaded partly via a substituting group and partly directly onto the dextrin backbone.

BRIEF DESCRIPTION OF THE DRAWINGS

An embodiment of the invention will now be described by example only and with reference to the following tables and figures;

Table 1 represents the characteristics of different batches of succinoylated dextrin doxorubicin conjugates;

Figure 1:
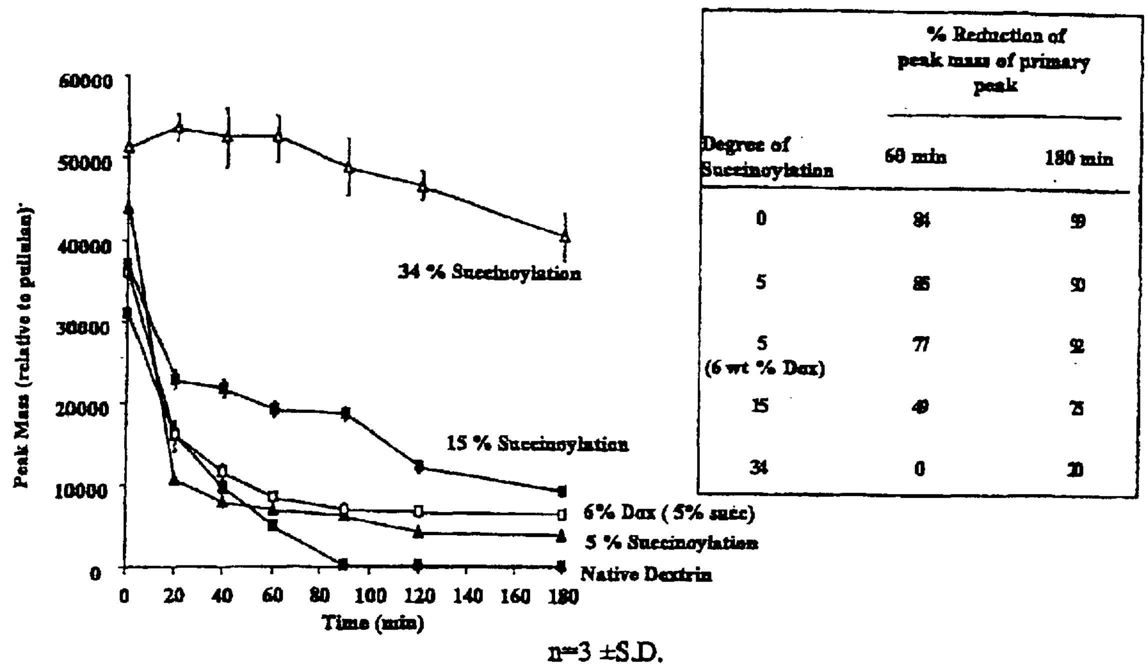
Figure 2:
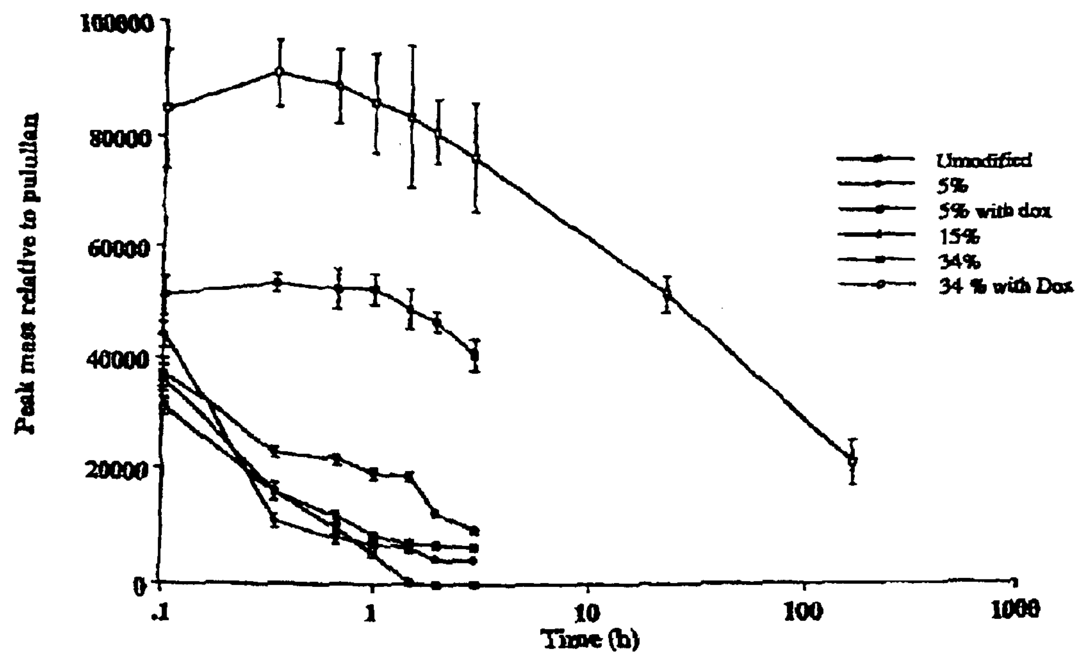
Figure 3:
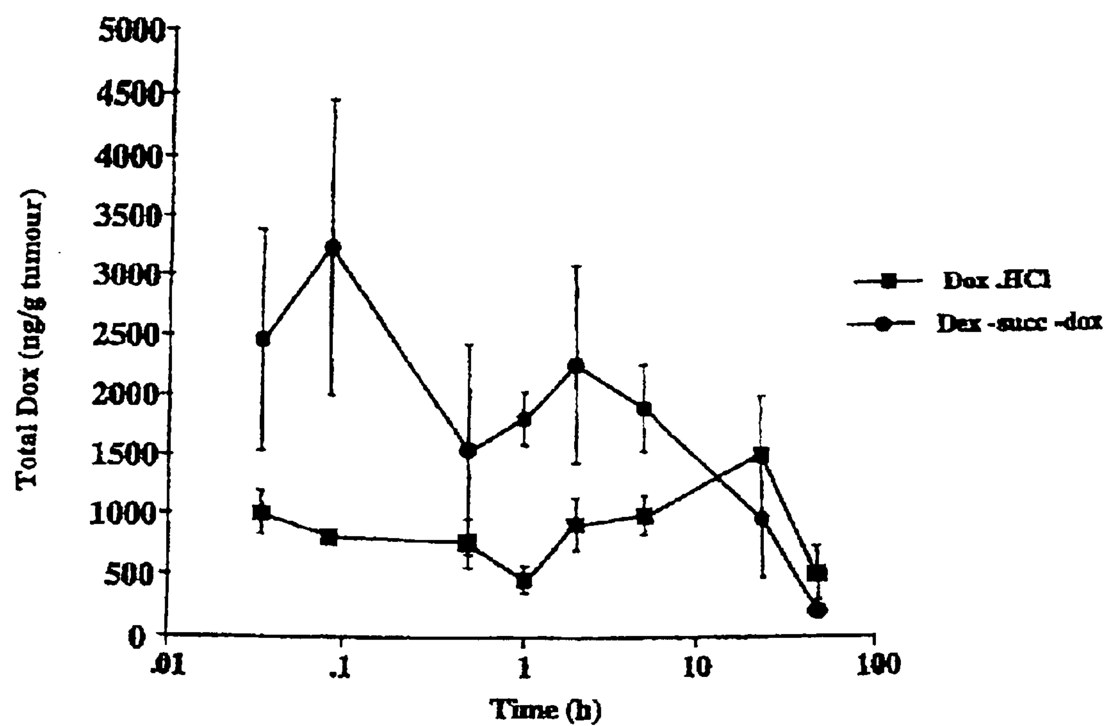
Figure 4:
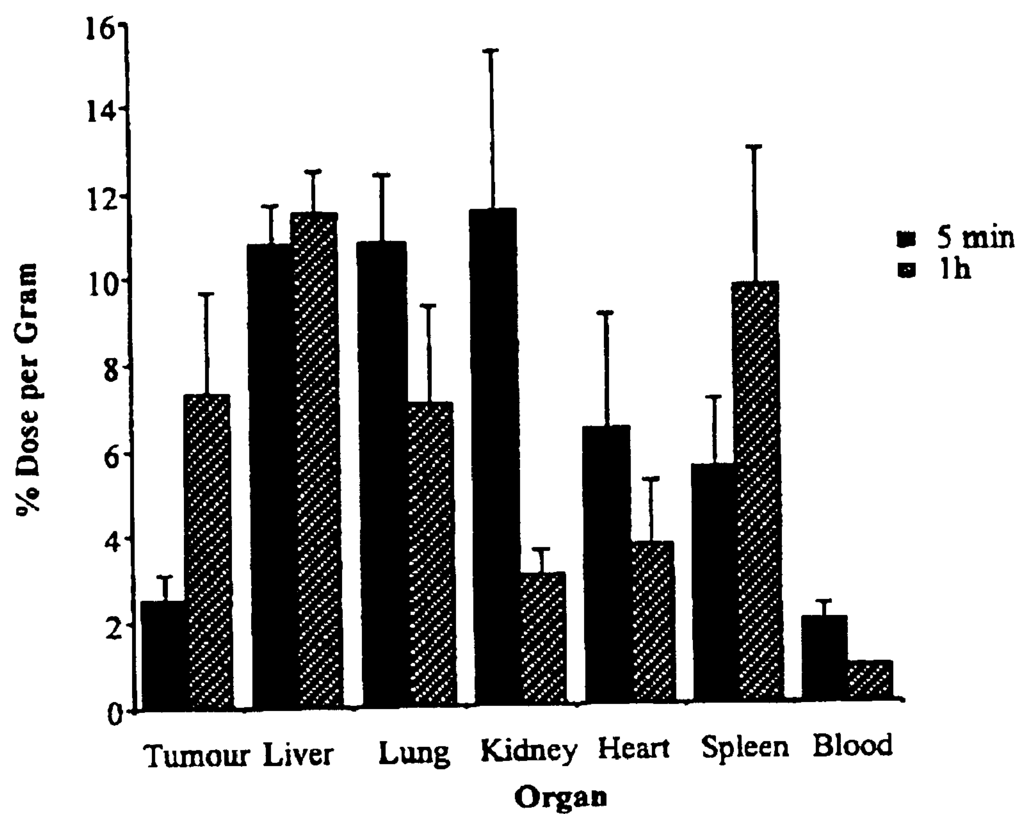
Figure 7:
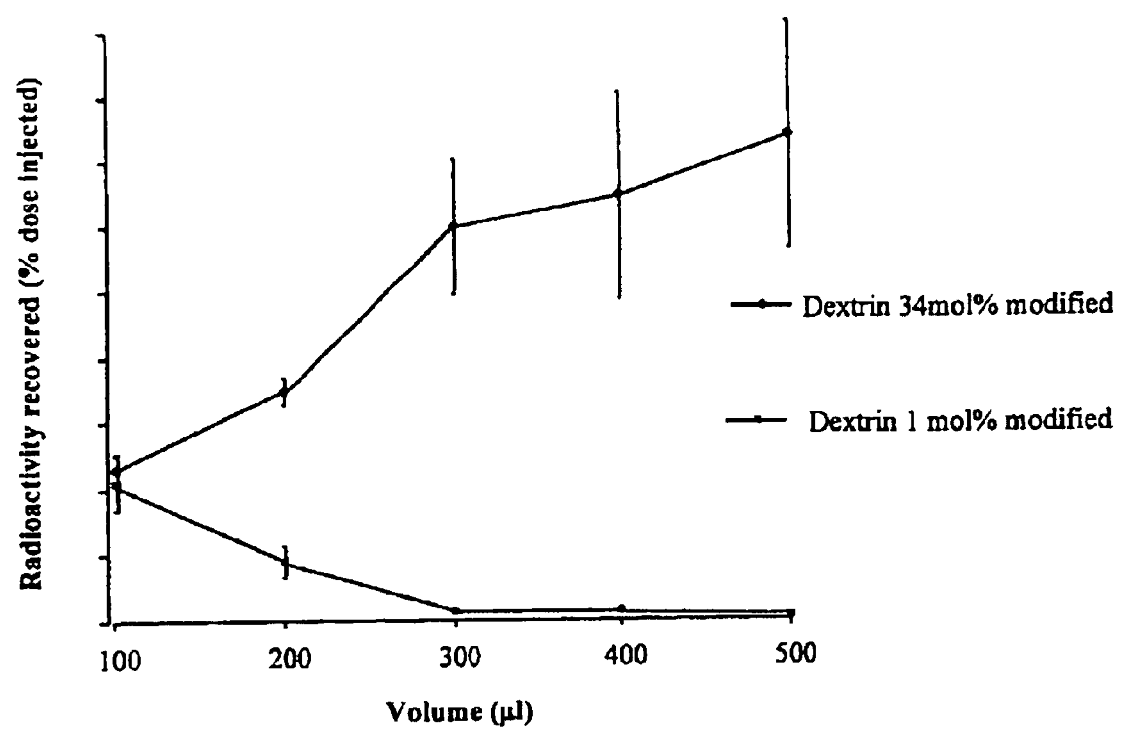

Table 2 shows the anticancer activity of succinoylated dextrin doxorubicin conjugates;

FIG. 1 is a graphical representation of the degradation of dextrin, succinoylated dextrin and a succinoylated dextrin doxorubicin conjugate (5% succinoylation, 6% doxorubicin);

FIG. 2 is a graphical representation of the degradation of hyper-succinoylated dextrin doxorubicin(34% succinoylation) conjugate with time;

FIG. 3 is a graphical representation of the preferential accumulation of succinoylated dextrin doxorubicin conjugate compared to an unconjugated control;

FIG. 4 illustrates the effect of the degree of dextrin succinoylation on biodistribution of $^{125}$I-labelled Dextrin at 34 mol % after i.v. administration;

FIG. 5 illustrates a comparison of the 1 and 34 mol % modified $^{125}$I-labelled dextrin at 5 min post i.v administration;

FIG. 6 illustrates a comparison of the 1 and 34 mol % modified $^{125}$I-labelled dextrin at 1 hr post i.v administration; and FIG. 7 represents the presence of $^{125}$I-labelled dextrin in the peritoneal wash after i.p. administration at 1 hr

DETAILED DESCRIPTION OF THE INVENTION

EXAMPLE 1

Dextrin (Mw 51,000 Da) was succinoylated using a modification of the method described by Bruneel et al (Polymer, 35 (12),(1994), 2656–2658). Doxorubicin was then conjugated directly via an amide bond, conjugated via an N-cis-aconityl spacer or conjugated via a glycyl-N-cis-aconityl spacer.

Polymer degradation (unmodified dextrin, succinoylated dextrin (5, 15 mol %) and conjugate) was measured in the presence of amylase or lysosomal enzymes to monitor either changes in polymer molecular weight (GPC) or doxorubicin release (HLPC).

The dextrin-doxorubin conjugates had a doxorubicin loading of 6–12 wt % dependent on the reaction conditions used and the degree of succinoylation of the dextrin intermediate. Table 1 shows the characteristics of several batches of dextrin-succ-doxorubicin.

TABLE 1

Characteristics of batches of dextrin-succ-doxorubicin

| Batch No | Dox (wt %) | Free Dox (% total Dox) |
|---|---|---|
| 1 | 11.7 | 0.8 |
| 2 | 11.9 | 2.0 |
| 3 | 8.7 | 1.2 |
| 4 | 8.4 | 0.1 |

After a 180 min incubation with amylase, unmodified dextrin is almost completely degraded to low molecular products, whilst the succinoylated dextrin (5 and 15 mol %) and dextrin-succ-doxorubicin show a biphasic pattern of degradation giving rise to fragments of Mw 4,000, 9,500 and 6,400 Da respectively. Unmodified dextrin had a $t_{1/2}$ (time for mass to reach half of its original) of 20 min, succinoylated dextrin and dextrin-succ-doxorubicin a $t_{1/2}$ of approximately 15 min.

EXAMPLE 2

In this example the degradation of dextrins of different degrees of modification was compared. The results are shown in FIG. 1. It will be seen that native dextrin is rapidly degraded as are also dextrin with 5% succinoylation (whether with or without 6% Dox) and dextrin with 15% succinoylation. However, if dextrin is 34% succinoylated the degree of degradation is markedly less, there being zero % reduction of the peak mass of primary peak after 60 minutes and only 20% reduction after 180 minutes. In addition, FIG. 2 shows that 34% succinoylated dextrin doxorubicin conjugate is similarly stable over an extended time course when compared to unconjugated or low level succinoylated (5%) controls.

EXAMPLE 3

In this example increased uptake of 34% succinoylated dextrin-doxorubicin by tumour cells is shown. Male C57 were injected with $10^6$ B16F10 murine melanoma cells subcutaneously with either doxorubicin hydrochloride or dextrin-succinoyl-doxorubicin (34 mol % succinoylation, 11.8% doxorubicin) at 5 mg/kg doxorubicin equivalence into the intrapertinoneal cavity (i.p.).

The mice were then culled after 2, 5, and 30 mins and after 1, 2, 5, 24, and 48 hours. Tumours were removed and weighed. The tumour was then homogenised and doxorubicin extracted and quantified by HLPC for total doxorubicin present, FIG. 3.

FIG. 3 shows there is approximately a three fold increase in tumour levels of doxorubicin were found for the conjugate for all time intervals from 2 min up to 24 hours. After this period, there is no difference between conjugate or the free drug. The elevated levels of the conjugate were at their highest 5 min after injection.

EXAMPLE 4

In this example the pharmacology of succinolyated dextrin doxorubicin is determined and is presented in Table 2. Twenty four C57 black mice were injected subcutaneously (s.c.) with $10^5$ B16F10 murine melanoma cells as described above and then monitored daily for well-being and the presence of palpable tumours. When the tumours were palpable, mice were randomly assigned into groups of six and their tumours measured with a micrometer gauge. Tumour size and mouse body weight is recorded. Each group is then injected intra-peritoneally with either sterile saline (negative control), free doxorubicin (5 mg $kg^{-1}$) in sterile saline or dextrin-doxorubicin (11.8 wt %, 34% succinolyation) at either 5 mg $kg^{-1}$ or 10 mg $kg^{-1}$, on days 0,1 and 2. The mice were monitored daily and tumour size and body weight recorded. Once the tumour area exceeded 2.89 $cm^2$ the mice were culled according to UKCCCR guidelines. Mouse survival is then expressed as % T/C (test/control saline).

The animals treated with doxorubicin (5 mg $kg^{-1}$) displayed a drop in body weight consistent with toxicity. However all mice tolerated the dextrin-doxorubicin conjugate at both doses. The higher dose (10 mg $kg^{-1}$) equates to approximately 2 mg of conjugate. As shown in Table 2, dextrin-doxorubicin conjugate resulted in a T/C of approximately 140% indicating anticancer activity. In contrast, free doxorubicin was not active in this experiment.

EXAMPLE 5

The tumour model used was B16F10 murine melanoma. Viable tumour cells ($10^5$) were injected subcutaneously into C57/BL mice near the base of the neck. When tumours were visible $^{125}$I-labelled dextrin (100 μl, $5\times10^5$ (cpm) was injected i.v. into the tail vein and the mice were culled at 5 min and 1 h. A blood sample was taken and the mouse weighed. The major organs were removed and homogenised in a known volume of DI water. Samples (3×1 ml) of each tissue were taken and assayed radioactivity. The total amount of radioactivity per organ was expressed as the percentage of the injected dose or as percent of the dose injected per gram of organ.

FIG. 4 shows the effect of the degree of dextrin succinoylation on biodistribution of $^{125}$I-labelled Dextrin at 34 mol % after i.v. administration. Over time it can be noted that there is an decrease in the overall % recovery of the injected dose. Example of organ recoveries, tumour levels increased from 2.5% dose (5 min) to 7.3% dose (1 h). Liver levels increased from 10.8% dose (5 min) to 11.5% dose (1 h) and spleen levels increased from 5.5% dose (5 min) to 9.7% dose (1 h). All of the other organs showed a decrease in the % recovery.

EXAMPLE 6

FIG. 5 shows a comparison of the 1 and 34 mol % modified $^{125}$I-labelled dextrin at 5 min. At five minutes the overall recovery is greatest in the 34 mol %, the tumour % recovery rose from 0.6% dose to 2.5% dose after an increased succinoylation and there was over a two fold difference in the other major organs except the kidney where the % recovery dropped from 15.7% to 11.5% of the injected dose.

EXAMPLE 7

FIG. 6 shows a comparison of the $^{125}$I-labelled dextrin at 1 h. At 1 h the accumulation in the kidneys is greater than at 1 mol % modified dextrin the 34 mol % giving 7.3% dose. The overall recovery for both mol % modified dextrin has decreased over time.

EXAMPLE 8

FIG. 7 show comparisons of recovery in the i.p. wash in the tumour bearing mice. The dextrin at 34 mol % is being retained in the i.p. cavity for longer than the other modified polymers

TABLE 2

| Compound | Dose mg $kg^{-1}$ (day 0,1,2) | Days survival after treatment (mean ± SD) | T/C (%) | Toxic deaths |
|---|---|---|---|---|
| Control (saline) | — | 4.3 ± 0.5 | 100 | 0/6 |
| doxorubicin | 5 | 4.5 ± $0.5^{ns}$ | 103 | 0/6 |
| Dextrin-Dox | 5 | 6.2 ± 0.8* | 142 | 0/6 |
| Dextrin-Dox | 10 | 6.0 ± 1.1** | 138 | 0/6 |

N = 6
$^{ns}$ = not significant
*p = 0.0004
**p = 0.005

What is claimed is:

1. A polymer drug conjugate comprising:

at least one anti-cancer agent; and a dextrin polymer, wherein said dextrin polymer is modified by succinoylation by at least 30 mol % characterised in that the stability of the polymer drug conjugate is enhanced.

2. The polymer drug conjugate according to claim 1, wherein said dextrin is succinoylated from 30% to 40 mol %.

3. The polymer drug conjugate according to claim 2, wherein said dextrin is succinoylated from 32% to 36 mol %.

4. The polymer drug conjugate according to claim 3, wherein said dextrin is succinoylated to about 34 mol %.

5. The polymer drug conjugate according to claim 1, wherein the percentage of α-1–6 linkages in the dextrin is less than 10%.

6. The polymer drug conjugate according to claim 5, wherein the percentage of α 1–6 linkages in the dextrin is less than 5%.

7. The polymer drug conjugate according to claim 1, wherein the molecular weight of the dextrin is in an average molecular weight range 1000–200000.

8. The polymer drug conjugate according to claim 7, wherein the molecular weight of the dextrin is in an average molecular weight range 2000–55000.

9. The polymer drug conjugate according to any of claim 1, wherein the dextrin contains more than 15% of polymers of DP greater than 12.

10. The polymer drug conjugate according to claim 9, wherein the dextrin contains more than 50% of polymers of DP greater than 12.

11. A polymer drug conjugate according to claim 1, wherein said anti cancer agent is selected from the group consisting of: cyclophosphamide; melphalan; carmusline; methotrexate, 5-fluorouracil; cytarabine; mercaptopurine; anthracyclines; daunorubicin, doxorubicin; epirubicin; vinca alkaloids; vinblastin; vincristine; dactinomycin; mitomycin C; taxol; L-asparaginase; G-CSF; cisplatin; and, optionally, carboplatin.

12. A pharmaceutical composition, comprising the polymer drug conjugate according to claim 1 and a pharmaceutically acceptable diluent, excipient or carrier.

13. A polymer drug conjugate comprising:

at least one biologically active agent; and a dextrin polymer, wherein said dextrin polymer is modified by succinoylation by at least 30 mol % characterised in that the stability of the polymer drug conjugate is enhanced.

14. The polymer conjugate according to claim 13, wherein said agent is an imaging agent.

15. The polymer conjugate according to claim 14, wherein the imaging agent is tyrosinamide.

16. The polymer conjugate according to claim 13, wherein said agent is a diagnostic agent.

17. The polymer conjugate according to claim 13 wherein said agent is a targeting agent.

18. The polymer conjugate according to claim 17 wherein the targeting agent is biotin.

19. A method for treating a cancer in an animal subject, comprising administering to the animal a pharmaceutically effective amount of the polymer drug conjugate according to claim 1, thereby treating the cancer in the subject.

20. The method according to claim 19 wherein said animal is human.

* * * * *